(12) United States Patent
Swaminathan et al.

(10) Patent No.: US 7,622,599 B2
(45) Date of Patent: Nov. 24, 2009

(54) ISOLATION AND PURIFICATION OF CAROTENOIDS FROM MARIGOLD FLOWERS

(75) Inventors: Sethuraman Swaminathan, Bangalore (IN); Kunhiraman Priya Madavalappil, Bangalore (IN)

(73) Assignee: Katra Phytochem Private Limited, Bangalore (IN)

( * ) Notice: Subject to any disclaimer, the term of this patent is extended or adjusted under 35 U.S.C. 154(b) by 83 days.

(21) Appl. No.: 11/667,285

(22) PCT Filed: Apr. 25, 2005

(86) PCT No.: PCT/IN2005/000123

§ 371 (c)(1),
(2), (4) Date: May 8, 2007

(87) PCT Pub. No.: WO2006/114794

PCT Pub. Date: Nov. 2, 2006

(65) Prior Publication Data

US 2008/0051591 A1    Feb. 28, 2008

(51) Int. Cl.
*C11B 1/10*    (2006.01)
(52) U.S. Cl. .................... 554/20; 554/8; 554/12
(58) Field of Classification Search ............ 554/8, 554/12, 20
See application file for complete search history.

(56) References Cited

U.S. PATENT DOCUMENTS

| | | | | |
|---|---|---|---|---|
| 5,382,714 | A | * | 1/1995 | Khachik ................ 568/834 |
| 5,648,564 | A | * | 7/1997 | Ausich et al. ............. 568/834 |
| 6,380,442 | B1 | | 4/2002 | Madhavi et al. |
| 6,504,067 | B1 | | 1/2003 | Montoya-Olvera et al. |
| 6,743,953 | B2 | | 6/2004 | Kumar et al. |
| 7,173,145 | B2 | | 2/2007 | Khachik |

FOREIGN PATENT DOCUMENTS

| | | |
|---|---|---|
| CN | 1120565 | 4/1996 |
| JP | 11-322708 | * 11/1999 |
| JP | 11322708 | 11/1999 |
| WO | 03048284 A1 | 6/2003 |

OTHER PUBLICATIONS

Brazana, E. et al., Enzyme-Mediated solvent Extraciton of Carotenoids form Marigold Flower (*Tagetes erecta*), 2002, Journal of Agric. Food Chem., vo. 50. No. 16, pp. 4491.*
Kyowa Hakko Kogyo Co. Ltd. JP 11-322708, 1999, (English translation 8 pages).*
Moeller et al., "The Potential Role of Dietary Xanthophyllis in Cataract and Age-Related Macular Degeneration" Journal of the American College of Nutrition, vol. 19, No. 5, 522S-527S (2000).
Hininger et al., "No Significant Effects of Lutein, Lycopene or B-Carotene Supplementation on Biological Markers of Oxidative Stress and LDL Oxidizability in Health Adult Subjects" Journal of the American College of Nutrition, vol. 20, No. 3, 232-238 (2001).
Chopra et al., "Effect of lutein on oxidation of low-density lipoproteins (LDL) in vitro" Proceedings of the Nutrition Society, 53 p 18A.
Britton, "Structure and properties of carotenoids in relation to function" FASEB J 9, 1551-1558 (1995).
Pfander, "Carotenoids: An Overview" Methods In Enzymology, vol. 213 (1992).
Howard et al., "Do Hydroxy-Carotenoids Prevent Coronary Heart Disease? A Comparison Between Belfast and Toulouse" Internat. J. Vit. Nutr. Res. 66, 113-118 (1996).
Chew et al., "Effects of Lutein from Marigold Extract on Immunity and Growth of mammary Tumors in Mice" Anti Cancer Research 16, 3689-3694 (1996).
Ong et al., "Natural Sources of Carotenoids from Plants and Oils" Methods In Enzymology, vol. 213 (1992).
Mercandate, "New carotenoids: Recent progress" Pure Appl. Chem., vol. 71, No. 12, pp. 2263-2272 (1999).

* cited by examiner

*Primary Examiner*—Porfirio Nazario-Gonzalez
*Assistant Examiner*—Yate' K Cutliff
(74) *Attorney, Agent, or Firm*—Sughrue Mion, PLLC

(57) ABSTRACT

The present invention explains a realistic and effective process for isolating and purifying carotenoids containing higher concentrations of carotenoids such as trans-lutein, trans-zeaxanthin, Cis-lutein, β-carotene and Cryptoxanthin from Marigold flower petals under controlled conditions leaving no traces of any organic hazardous solvents. The process involves ensilaging Marigold flowers, dehydration, solvent extraction, alkali hydrolysis of carotenoid esters with absolute alcohol, crystallization/purification using water, absolute alcohol mixture followed by filteration and drying until the crystals are considerably free from moisture and absolutely free from residual hazardous solvents. These crystals are suitable for nutraceutical and food products as supplements.

18 Claims, No Drawings

ISOLATION AND PURIFICATION OF CAROTENOIDS FROM MARIGOLD FLOWERS

FIELD OF THE INVENTION

The present invention relates to pure carotenoid crystals derived from Marigold flowers and particularly to their isolation and purification process.

BACKGROUND OF THE INVENTION

Pure carotenoid crystals derived from Marigold flowers, comprising predominantly of Xanthophylls such as Lutein, Zeaxanthin and Cryptoxanthin and low levels of carotene have been proven scientifically to reduce the risk of age related macular degeneration (Reference: Moeller S M, Jacques P F, Blumberg J B "The potential role of dietary Xanthophylls in cataract and age related macular degeneration," Journal of the American College of Nutrition, 2000; 19:522S-527S), control over LDL cholesterol (Reference: Chopra M., Thumham D I, "Effect of Lutein on oxidation of low density lipoproteins (LDL) in vitro", Proceedings of the Nutrition Society, 1994; 53: 1993, #18A), prevention of Coronary heart diseases (Reference: Howard A N, Williams N R, Palmer C R, Cambou J P, Evans A E, Foote J W, et al., "Do hydroxy-carotenoids prevent coronary heart disease?" A comparison between Belfast and Toulouse, "*International Journal of Vitamin and Nutrition Research,* 1996; 66: 113-118) and free radicals scavenging and immunity enhancing (Reference: Chew B P, Wong M W, Wong T S, "Effects of Lutein from Marigold extract on immunity and growth of mammary tumors in mice," *Anticancer Research,* 1996; 16: 3689-3694).

Lutein, (β-ϵ-carotene-3-3-diol) and Zeaxanthin (β-β-carotene-3-3'-diol) belong to Xanthophylis group in the carotenoids family with highly reactive hydroxyl groups which cannot be synthesized by humans and animals.

Carotenoids are a class of natural fat-soluble pigments found principally in plants, algae, and photosynthetic bacteria, where they play a critical role in the photosynthetic process. They also occur in some non-photosynthetic bacteria, yeasts, and molds, where they may carry out a protective function against damage by light and oxygen. Although animals appear to be incapable of synthesizing carotenoids, many animals incorporate carotenoids from their diet. Within animals, carotenoids provide bright coloration, serve as antioxidants, and can be a source for vitamin A activity (Ong and Tee 1992; Britton et al. 1995).

Carotenoids are responsible for many of the red, orange, and yellow hues of plant leaves, fruits, and flowers, as well as the colors of some birds, insects, fish, and crustaceans. Some familiar examples of carotenoid coloration are the oranges of carrots and citrus fruits, the reds of peppers and tomatoes, and the pinks of flamingoes and salmon (Pfander 1992). Some 600 different carotenoids are known to occur naturally (Ong and Tee 1992), and new carotenolds continue to be identified (Mercadante 1999).

Carotenoids are defined by their chemical structure. The majority carotenoids are derived from a 40-carbon polyene chain, which could be considered the backbone of the molecule. This chain may be terminated by cyclic end-groups (rings) and may be complemented with oxygen-containing functional groups. The hydrocarbon carotenoids are known as carotenes, while oxygenated derivatives of these hydrocarbons are known as xanthophylls. Beta-carotene, the principal carotenoid in carrots, is a familiar carotene, while Lutein, the major yellow pigment of marigold petals, is a common xanthophyll.

The structure of a carotenoid ultimately determines what potential biological function(s) that pigment may have. The distinctive pattern of alternating single and double bonds in the polyene backbone of carotenoids is what allows them to absorb excess energy from other molecules, while the nature of the specific end groups on carotenoids may influence their polarity.

The former may account for the antioxidant properties of biological carotenoids, while the latter may explain the differences in the ways that individual carotenoids interact with biological membranes (Britton 1995).

U.S. Pat. No. 5,382,714 reports that saponified marigold oleoresin from Kemin Industries (Des Moines, Iowa) containing free lutein is the preferred starting material for the isolation of pure lutein. The saponification step involves high percentage of propylene glycol and the saponification time is done for a minimum period of three hours subjecting the product to heat for prolonged period, which increases the process time too.

U.S. Pat. No. 5,648,564 uses aqueous alkali and propylene glycol wherein the Carotenoid esters are neither soluble nor freely miscible with them and hence it requires very long time at higher temperature for the fatty esters to saponify which may result in exposure of the product for a longer duration under heat and air, promoting the formation of oxidative degenerative products and the process time is too long for a commercial batch.

U.S. Pat. No. 6,743,953 describes final purification step involving multiple solvents like ethyl acetate, hexane, acetone and methanol with the possibilities of leaving residues of the same. Again the process involves saponification upto 3 hrs. Subjecting the product to heat at 70° C. for more time which may result in degenerated oxidative products in the saponified mass.

U.S. Pat. No. 6,380,442 states that the hydrolysis of carotenoids is done by using iso propyl alcohol with saponification time being 90 minutes.

U.S. Pat. No. 6,504,067 states that the Marigold oleoresin is pre treated with Sodium Carbonate and further neutralisation with dilute Phosphoric acid, prior to taking it to saponification reaction using aqueous alkali and carried out the saponification at a temperature at 90° C. for 8 hours. Subsequently the reaction mass is subjected to readjustment of pH with acetic acid to 5.0, and washing the residues with excess water in order to bring the pH to neutral. The disadvantage in the process is that the product is subjected to heat for a prolonged period and too many steps of acidification and neutralisations are involved to remove the impurities.

BRIEF SUMMARY OF THE INVENTION

The present invention is realistic and effective process to isolate carotenoids, predominantly, Lutein from marigold flower petals (as the preferred source). The process involves ensilaging marigold flower petals under controlled anaerobic conditions to fix and enrich the carotenoids present in the petals, dehydration involving couple of steps like screw press, shredding and fluidised bed drying using eco friendly producer gas as heating medium for the drier without any hazardous stack emission to obtain dried meal. The dried meal is then pelletised to convenient size, density and hardness to facilitate better extractability of the carotenoid esters. The pellets are solvent extracted using food grade hexanes and are stripped for solvent to the least possible extent without much degradation in the oleoresin.

The oleoresin is then homogenized with absolute alcohol before the addition of alkali and the esters are saponified at temperature between 70° C. and 80° C. for a maximum time of 30 minutes only. The hydrolyzed carotenoids are then precipitated using a mixture of water and alcohol and washed with hot water for the removal of all unwanted trace impurities. The washed crystals are then filtered using Centrifuge and then dried either under vacuum or under atmospheric pressure to remove moisture and volatile organic impurities, if any.

The advantages of the present invention is that the carotenoid esters can be saponified within 30 minutes duration only upto more than 99% saponification and the product is not subjected to heat for a longer duration which may result in the formation of degenerated oxidative products. The saponified mass is immediately precipitated with the aid of alcohol-water mixture under slightly warm conditions aiding the removal of most of the unwanted and unreacted impurities in a single step. The whole process of homogenisation, saponification, precipitation, washing and filtration can be completed within a time span of 3 hours.

The present invention has advantage in its time-temperature combination, simplicity of procedure and usage of low amounts of solvents. All these factors contribute towards the yield and stability of the product and bring down the cost of production on a commercial scale.

DETAILED DESCRIPTION OF THE INVENTION

The present invention is realistic and effective process to isolate and purify carotenoids from Marigold flower petals, comprising predominantly Lutein. The cultivar *Tagetes erecta* is cultivated under dedicated package of practices including seed production, harvested and brought to the dehydration unit within hours of harvest. The package of practices includes non-GMO seed development and cultivation suiting tropical conditions. The flowers are then immediately taken for silaging in silos after physical cleaning and sprayed with anti oxidant and silage additive at appropriate concentration under dosed anaerobic conditions.

The silaging is monitored through pH and temperature of the silage and ensured for complete fermentation over a period of two to three weeks.

The silaged flowers are then harvested from the silos and subjected to dehydration process in series of steps. The silaged flowers are subjected to industrial screw press in two stages and are squeezed for the oozing water, bringing the moisture content from 88% to 75%. The squeezed flowers are then subjected to shredding before it is dried in fluid bed drier. The shredded flowers are dried in a fluid bed drier using hot air, generated by heating air with producer-gas flame produced by using an eco-friendly gassifier with absolutely stack free emission. The tunnel type industrial fluid bed drier comprises of drying chambers with different temperatures across the tunnel from inlet, being the maximum temperature (85° C. to 90° C.) to the outlet at temperature (45° C. to 50° C.).

The transit time inside the FBD from inlet to outlet is only 30 minutes maximum, wherein the moisture level in the product is brought down to around 10% from 75%. The advantage in this drying process is that the product is not subjected to high heat for longer duration, minimising the formation of degenerative oxidative products that could form due to heat and air for prolonged periods.

The dried Marigold meal is pulverised using an industrial hammer mill and down sized to particles less than 400 microns.

The ground Marigold meal is pelletised to 6 mm to 10 mm size pellets using an industrial pelletiser to the desired bulk density with the aid of steam/hot water as binder.

The Marigold flower pellets are subjected to solvent extraction using food grade Hexanes as solvent in a battery of extractors under counter current extraction to achieve maximum extractability of active principles viz., Xanthophylls and carotenoids along with the other resinoids and lipids. The lean miscella is then concentrated in Falling film evaporators and Wiped film evaporators to bring down the solvent concentration to around 5% from 90% to 95% approximately. The concentrated miscella is then subjected to vacuum distillation to bring down the solvent level from 5% to 1%. This crude Marigold Oleoresin with 1% solvent level in it, is further concentrated by stripping the solvent under a stream of Nitrogen and Steam to reduce the solvent levels to less than 1000 ppm in the final Marigold oleoresin. Throughout the concentration operation the product is not subjected to temperatures more than 60° C. at any given point of time, minimising the formation of oxidative degenerated products like Epoxides.

The Marigold oleoresin obtained is homogenised in a reactor under stirring at a temperature not exceeding 45° C. for a period of maximum 10 minutes.

The homogenised Marigold oleoresin is then hydrolized in the same reactor with the addition of 1.2 to 2.0 volumes of 13% to 15% alcoholic Potassium Hydroxide solution, of the quantity of the Marigold oleoresin, at a temperature ranging between 70° C. and 80° C. for a time period of not more than 30 minutes wherein the alcohol used is absolute Ethyl alcohol with moisture content less than 5%. The degree of saponification is ensured by either Thin layer chromatography or High pressure liquid chromatography and the final cooking is done for 10 minutes at the same temperature after ensuring the completion of saponification more than 99%.

To the saponified mass, hot water generated in a separate vessel at a temperature of 65° C. to 75° C. is added and homogenised well for 10 minutes at the same temperature to aid the crystallisation of Carotenoids in the mixture of water and absolute alcohol in the ratio of 1:1, wherein the ratio of Ethyl alcohol to water at 50:50, promotes better crystallisation of Carotenoids and as well dissolves the unwanted impurities like soaps, lipids, fats and other organic matters.

The diluted mass is then filtered through a filter press by pumping the mass into the filter press aided by positive pressure using either Nitrogen or air. The collected mass inside the filter press plate is given with a hot water wash at a temperature of 60° C. to 70° C. with sufficient quantity of hot water until the pH is brought down to neutral at around 7.0.

The wet mass collected from the filter press is taken in trays in thin layers and dried in tray drier at a temperature between 50° C. and 55° C. at atmospheric pressure or in a vacuum tray drier at reduced pressure at a temperature between 40° C. and 45° C. for the time (usually 3 to 4 hours) until the moisture level in the product is less than 1% and any hazardous organic volatile impurity is below the detectable limit determined by Gas chromatography.

The resulting product contains a minimum of 90% Carotenoids determined by spectrophotometer and contains a minimum of 90% all trans-Lutein, 5 to 8% all trans-Zeaxanthin, less than 1% each of cis-Luteins, Beta carotene and Cryptoxanthin, determined by normal phase High pressure liquid chromatography.

The chemical recovery of the active principles viz., Carotenoids and Xanthophylls in the end product is between 55% and 80% depending upon the desired final product purity and the variable conditions thereof utilised based on the above process parameters by slight modifications of the process herein.

The finished product of carotenoid crystals obtained are formulated and stabilised in bulk, in the form of Powder, Beadlets, Granules, Oil dispersions and Water dispersions with concentrations varying from 1% to 40% concentrations by adding suitable pharma grade excipients and emulsifiers depending upon the end usage in line with the nutraceutical and food products applications.

While the invention has been described with reference to the explained embodiment, it is not limiting to anybody's skill to make various changes or equivalents without altering or departing from the main scope of this invention. Therefore, it is intended that the invention not be limiting to the embodiment described but will cover and include all other embodiments falling within the scope of the claims made herein.

The following examples are illustrative, but not limiting, of the methods and compositions of the present invention. Other suitable modifications and adaptations of the variables of the conditions and normally encountered in natural products isolation and purification techniques which are obvious to those skilled in the art are within the spirit and scope of the present invention.

Example 1

25 Kgs of Marigold Oleoresin having 92.19 gm/Kg or 9.22% of Xanthophylls is taken in 100 liters capacity reactor with an agitator. The Oleoresin is homogenised for 10 minutes under stirring at a temperature of 40° C. with either steam or hot water in the jacket of the reactor as heating medium. Ethanolic KOH is prepared by taking 5 Kgs of KOH with purity of 95% and dissolving it in 35 liters of Ethyl alcohol (1:1.4 volumes). The prepared ethanolic KOH is added into reaction vessel slowly, containing the homogenised mass. The saponification reaction is carried out at a temperature of 75° C. for 30 minutes. After ensuring the degree of saponification to be more than 99% by HPLC, 40 liters of demineralised hot water maintained at a temperature of 70° C. is added to the reacted mass and the stirring is continued for 10 minutes. The diluted mass with carotenoid crystals is then pumped into a filter press to recover the crystals. Around 250 liters of additional hot water is pumped through the filter press to wash the unwanted impurities and bring down the pH of the effluent to neutral around 7.0. After ensuring the neutralisation, positive pressure of Nitrogen is applied to the filter press at pressure 1.25 Kg to squeeze the crystals trapped inside the filter. The wet crystals are then collected from the filter press plates into trays in a thin layer and dried in a tray drier at a temperature around 55° C. for 3 hours under normal pressure.

The physical recovery of the final product is 6.76%. The Carotenoid crystals obtained contained 91.28% carotenoids (determined by spectrophotometer) of which 91.99% is all trans-Lutein, 6.90% all trans-Zeaxanthin, 0.27% cis-Luteins, 0.23% Beta Carotene and 0.5% Cryptoxanthin (determined by HPLC). The chemical recovery of the final product is 66.9%.

The final product contained a moisture content of 0.57% and could not be detected for any traces of residual hexanes by gas chromatography analysis.

Example 2

25.5 Kgs of Marigold Oleoresin having 102.18 gm/Kg or 10.22% of Xanthophylls is taken in 100 liters capacity reactor with an agitator.

The Oleoresin is homogenised for 10 minutes under stirring at a temperature of 45° C. with either steam or hot water in the jacket of the reactor as heating medium. Ethanolic KOH is prepared by taking 5.1 Kgs of KQH with purity of 95% and dissolving it 40 liters of Ethyl alcohol (1:1.56 volumes).

The prepared Ethanolic KOH is added into reaction vessel slowly, containing the homogenised mass. The saponification reaction is carried out at a temperature of 73° C. for 30 minutes. After ensuring the degree of saponification to be more than 99% by HPLC, 45 liters of demineralised hot water maintained at a temperature of 65° C. is added to the reacted mass and the stirring is continued for 10 minutes. The diluted mass with carotenoid crystals is then pumped into a filter press to recover the crystals. Around 275 liters of additional hot water is pumped through the filter press to wash the unwanted impurities and bring down the pH of the effluent to neutral around 7.0. After ensuring the neutralisation, positive pressure of Nitrogen is applied to the filter press at pressure 1.2 Kg to squeeze the crystals trapped inside the filter. The wet crystals are then collected from the filter press plates into trays in a thin layer and dried in a tray drier at a temperature around 45° C. for 2 hours under vacuum at 600 mm Hg.

The physical recovery of the final product is 7.67%. The Carotenoid crystals obtained contained 93.76% carotenoids (determined by spectrophotometer) of which 92.86% Is all trans-Lutein, 6.14% all trans-Zeaxanthin, 0.12% cis-Luteins, 0.22% Beta Carotene and 0.52% Cryptoxanthin (determined by HPLC). The chemical recovery of the final product is 70.53%.

The final product contained a moisture content of 0.63% and could not be detected for any traces of residual hexanes by gas chromatography analysis.

What is claimed is:

1. A method for producing carotenoids rich in Lutein from Marigold flower petals comprising the steps of:
   (a) ensilaging Marigold flower petals under controlled anaerobic conditions to fix and enrich the carotenoids present in the petals;
   (b) dehydration through eco friendly drying process to obtain dried meal;
   (c) pellatilizing the meal;
   (d) solvent extraction of the pellatilized meal using food grade hexanes to obtain carotenoid esters rich Marigold oleoresin;
   (e) hydrolysis of carotenoids esters with alcoholic alkali after homogenizing the oleoresin;
   (f) precipitation of carotenoid crystals using water alcohol mixture;
   (g) washing with sufficient quantity of hot water to remove water soluble soaps, chlorophyllins and other organic impurities like trace residual hexanes;
   (h) filteration of carotenoid crystals using filter press, centrifuge and neutch filter; and
   (i) drying to obtain pure carotenoid crystals having high purity levels, considerably low in moisture and absolutely free from residual hazardous solvents.

2. The method of claim 1, wherein said Marigold flowers are from *Tagetes erecta* species, grown from non-GMO seeds using cultivation practices suiting tropical conditions.

3. The method of claim 1, wherein the ensilaging in step (a) is done under anaerobic conditions using oxygen scavengers and sealants, minimizing the pigment loss due to formation of unwanted oxidation products.

4. The method of claim 1, wherein the dehydration through eco friendly drying process in step (b) is done using fluid bed dryers with a heating mechanism using producer gas generated by gassifiers, absolutely free from any hazardous stack emissions.

5. The method of claim 1, wherein the pellatizing in step (c) done using a suitable compactor to aid better solvent extraction.

6. The method of claim 1, wherein the solvent extraction in step (d) is done using food grade hexanes to obtain Marigold oleoresin containing minimum amount of residual solvents, using counter current extraction procedure to obtain maximum extractability of the carotenoids.

7. The method of claim 1, wherein the temperature in step (d) does not exceed more than 60° C., minimizing the oxidative degenerative products.

8. The method of claim 1, wherein the homogenization of oleoresin in step (e) at temperature not exceeding 45° C. for a period of 10 minutes.

9. The method of claim 1, wherein the hydrolysis of carotenoid esters in step (e) is done using Ethanolic potassium hydroxide.

10. The method of claim 1, wherein the hydrolysis temperature in step (e) is between 70° C. and 80° C. and the saponification time is not more than 30 minutes.

11. The method of claim 1, wherein the precipitation of carotenoid crystals in step (f) is done using absolute alcohol water mixture at 50:50 ratio.

12. The method of claim 1, wherein the washing in step (g) is done using hot water between 50° C. and 70° C. with a volume of around 15 times to ensure the product pH to be neutral with complete removal of trace alkali and unwanted hazardous trace impurities.

13. The method of claim 1, wherein the filteration of the purified carotenoid crystals in step (h) is done using filter press or centrifuge or neutch filter.

14. The method of claim 1, wherein the drying in step (i) is done at around 50° C.-55° C. at ambient pressure or 40° C.-45° C. under reduced pressure.

15. The method of claim 1, wherein the pure carotenoid crystals obtained after drying in step (i) contains moisture level less than 1% and no traces of residual hexanes.

16. The method of claim 1, wherein the pure carotenoid crystals obtained after drying in step (i) contains total carotenoids not less than 90% by spectrophotometry with not less than 90% trans-lutein, not less than 5% trans-zeaxanthin with less than 1% each of other carotenoids like, Cis-luteins, β-carotene and Cryptoxanthin by High Pressure Liquid Chromatography.

17. The method of claim 1, wherein the pure carotenoids obtained contains between 55% and 80% by weight of the total carotenoids in the Marigold oleoresin.

18. The method of claim 1, wherein the pure carotenoid crystals so obtained are formulated and stabilized in bulk, in the form of powder, beadlets, granules, oil dispersions and water dispersions.

* * * * *